US00PP33450P2

(12) United States Plant Patent
Nelson et al.

(10) Patent No.: US PP33,450 P2
(45) Date of Patent: Sep. 7, 2021

(54) STRAWBERRY PLANT NAMED 'BG-12.3266'

(50) Latin Name: ***Fragaria* x *ananassa***
Varietal Denomination: BG-12.3266

(71) Applicant: BERRY GENETICS, INC., Freedom, CA (US)

(72) Inventors: Steven D. Nelson, Watsonville, CA (US); Michael D. Nelson, Watsonville, CA (US); Leo W. Stoeckle, Moorpark, CA (US); Daniel S. Nelson, Watsonville, CA (US)

(73) Assignee: Berry Genetics, Inc., Freedom, CA (US)

( * ) Notice: Subject to any disclaimer, the term of this patent is extended or adjusted under 35 U.S.C. 154(b) by 0 days.

(21) Appl. No.: 16/990,826

(22) Filed: Aug. 11, 2020

(51) Int. Cl.
*A01H 5/08* (2018.01)
*A01H 6/74* (2018.01)

(52) U.S. Cl.
USPC ..... Plt./208

(58) Field of Classification Search
USPC ..... Plt./208, 209
CPC ... A01H 5/08; A01H 5/00; A01H 6/74; A01H 6/7409; A01H 5/02
See application file for complete search history.

(56) References Cited

U.S. PATENT DOCUMENTS

PP29,794 P2 * 11/2018 Nelson ..... Plt./209

OTHER PUBLICATIONS

Upov Pluto Plant Variety Database 20210123, retrieved on Feb. 1, 2021, retrieved from the Internet at https://www.upov.int/pluto/en/index.jsp, one page. (Year: 2021).*

* cited by examiner

*Primary Examiner* — June Hwu
(74) *Attorney, Agent, or Firm* — Foley & Lardner LLP

(57) ABSTRACT

This invention relates to a new and distinct variety of strawberry plant named 'BG-12.3266'. This new strawberry plant named 'BG-12.3266' is primarily adapted to the growing conditions of the central coast of California, and is primarily characterized by its orange red to red fruit color, medium fruit size, and cordate fruit shape, with very strong gloss; good fruit flavor, very firm fruit flesh, with seeds held even with the surface; very smooth fruit surface, even color, with only a slight difference between primary and secondary fruit; medium plant size, upright in habit, with medium density; medium yellow green foliage color, and medium foliage size; and fruit trusses typically held beneath the plant, with weak pubescence.

5 Drawing Sheets

Latin name of the genus and species of the plant claimed: *Fragaria* x *ananassa.*

Variety denomination: 'BG-12.3266'.

BACKGROUND OF THE INVENTION

The present invention relates to a new and distinct strawberry variety named 'BG-12.3266'. This new variety is a result of a controlled cross made in 2012 in an ongoing breeding program between strawberry variety designated 'BG-3.324' (U.S. Plant Pat. No. 23,256) as the seed (female) parent, and strawberry variety designated 'Florida Radiance' (U.S. Plant Pat. No. 20,363) as the pollen (male) parent. The variety is botanically known as *Fragaria* x *ananassa.*

The seedling resulting from the aforementioned cross was selected from a controlled breeding plot in Ventura County, Calif. in the winter of 2014. After its selection, the new variety was asexually propagated by stolons in both Siskiyou County, Calif. and San Joaquin County, Calif. The new variety was extensively tested over the next several years in fruiting fields in Ventura County, Calif. This propagation has demonstrated that the combination of traits disclosed herein as characterizing the new variety are fixed and remain true-to-type through successive generations of asexual reproduction.

BRIEF SUMMARY OF THE INVENTION

'BG-12.3266' is primarily adapted to the climate and growing conditions of the central coast of California. The nearby Pacific Ocean provides the humidity and moderate temperatures needed to produce a strong, vigorous plant and maintain fruit quality during the winter and spring production months.

The following traits have been repeatedly observed and are determined to be unique characteristics of 'BG-12.3266', which in combination distinguish this strawberry plant as a new and distinct variety:

1. Fruit ranges from orange red to red in color, medium in size, and cordate in shape, with very strong gloss;
2. Fruit has good flavor, very firm flesh, with seeds held even with the surface;
3. Fruit surface is very smooth, even in color, with only a slight difference between primary and secondary fruit;
4. Plant is medium in size, upright in habit, with medium density;
5. Foliage is medium yellow green in color, and medium in size; and
6. Fruit trusses are typically held beneath the plant, with weak pubescence.

The strawberry variety that is believed to be most closely related to the new variety 'BG-12.3266' is 'Inspire' (U.S. Plant Pat. No. 29,794). In side-by-side comparisons to the similar strawberry variety 'Inspire', 'BG-12.3266' differs by the following combination of characteristics as described in Table 1.

TABLE 1

| Characteristic | 'BG-12.3266' | 'Inspire' (U.S. Plant Pat. No. 29,794) |
|---|---|---|
| Fruit: color | Ranges from orange red to red | Orange red |
| Fruit: season average size (gm) | 28.5 | 26.6 |
| Fruit: market yield season (gm/plt) | 1,079 | 866 |
| Fruit: flavor | Good (2.4 out of 5) | Excellent (3.7 out of 5) |
| Terminal leaflet: shape of base | Obtuse | Acute |
| Foliage: shape in cross section | Strongly to slightly concave | Flat to slightly convex |
| Petiole: size (cm) | 13.4 | 10.2 |
| Petiole: pubescence | Heavy | Moderate |
| Fruiting truss: position relative to foliage | Beneath | Above |

For identification, a series of molecular markers have been determined for this new variety.

'BG-12.3266' differs from its parents, 'BG-3.324' and 'Florida Radiance' by the following combination of characteristics as described in Tables 2 and 3.

TABLE 2

| Characteristic | 'BG-12.3266' | 'BG3.324' (U.S. Plant Pat. No. 23,256) |
|---|---|---|
| Fruit: season average size | Medium | Large |
| Time of flowering: harvest maturity | Medium | Early |
| Fruit: firmness of flesh | Very firm | Firm |
| Fruiting truss: position relative to foliage | Beneath | Ranges from level with to above |

TABLE 3

| Characteristic | 'BG-12.3266' | 'Florida Radiance' (U.S. Plant Pat. No. 20,363) |
|---|---|---|
| Fruit: season average size | Medium | Small |
| Fruit: color | Ranges from orange red to red | Red |
| Fruit: shape | Cordate | Long conical |
| Plant: size | Medium | Ranges from medium to small |

BRIEF DESCRIPTION OF THE PHOTOGRAPHS

The accompanying color photographs illustrate the overall appearance of typical specimens of the new strawberry variety 'BG-12.3266' at various stages of development, as true as it is reasonably possible with color reproductions of this type. Color in the photographs may differ slightly from the color value cited in the botanical descriptions which accurately describe the color of 'BG-12.3266'. The depicted plant and plant parts of the new strawberry variety 'BG-12.3266' are approximately six months old. The photographs were taken in Ventura County, Calif.

DETAILED BOTANICAL DESCRIPTION

Figure 1:
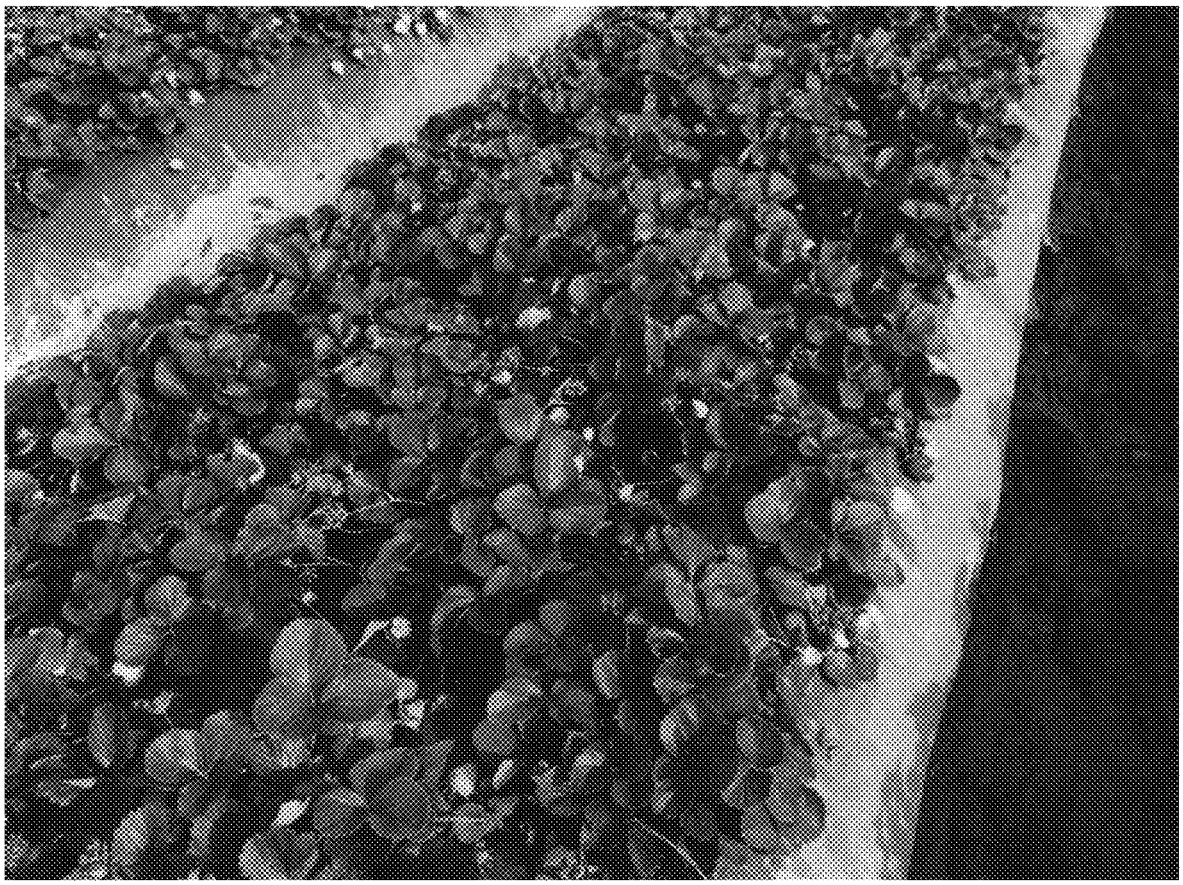
FIG. 1 shows fruiting field characteristics of 'BG-12.3266', taken in the month of April 2020.
Figure 2:
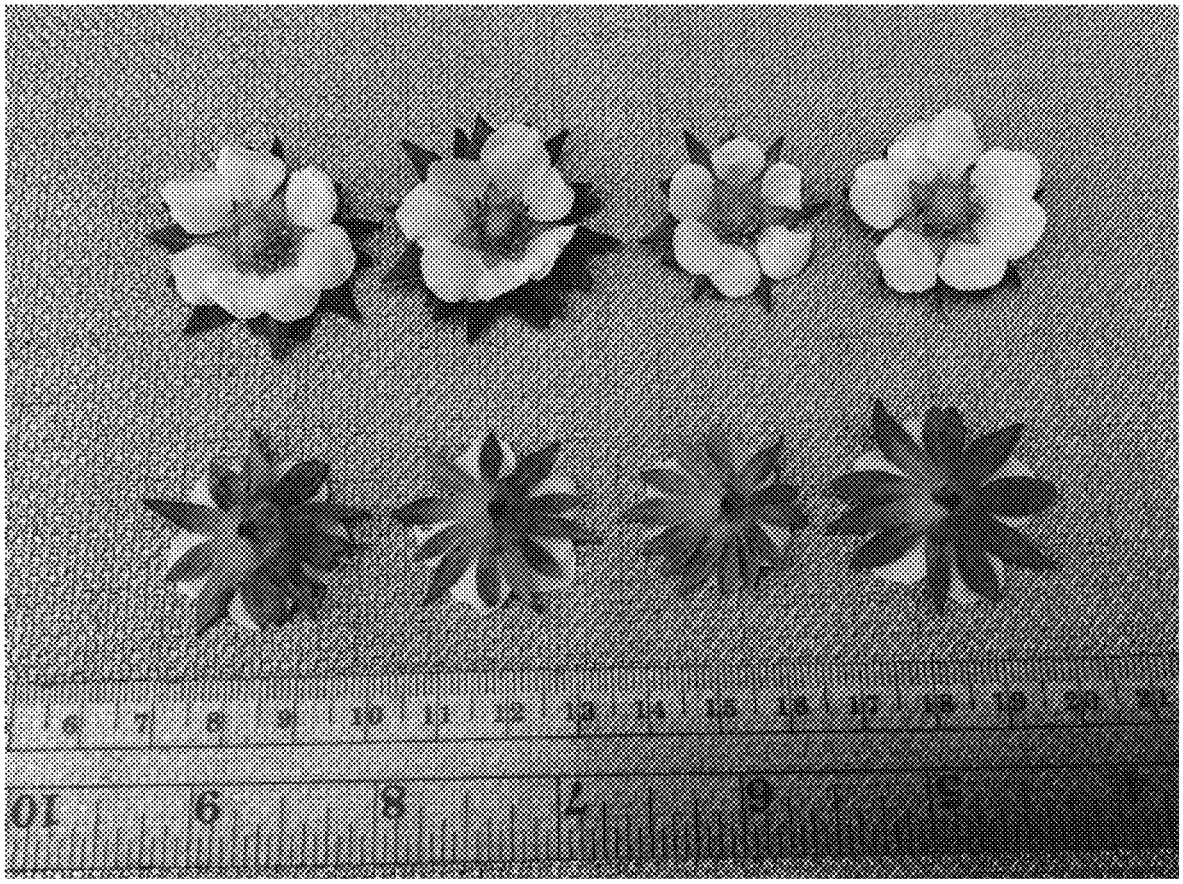
FIG. 2 shows upper and lower surfaces of flower and flower parts of 'BG-12.3266', taken in the month of April 2020.
Figure 3:
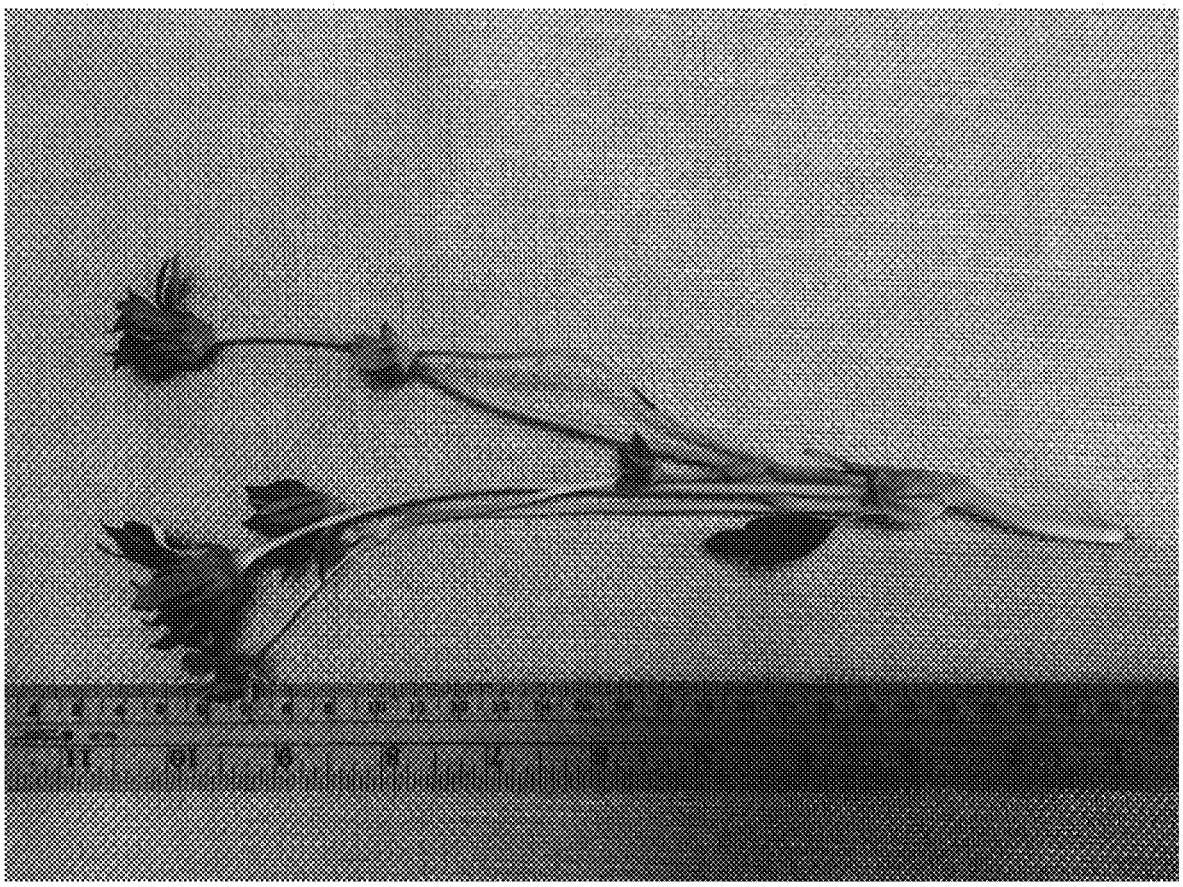
FIG. 3 shows typical fruiting truss and truss parts of 'BG-12.3266', taken in the month of April 2020.
Figure 4:
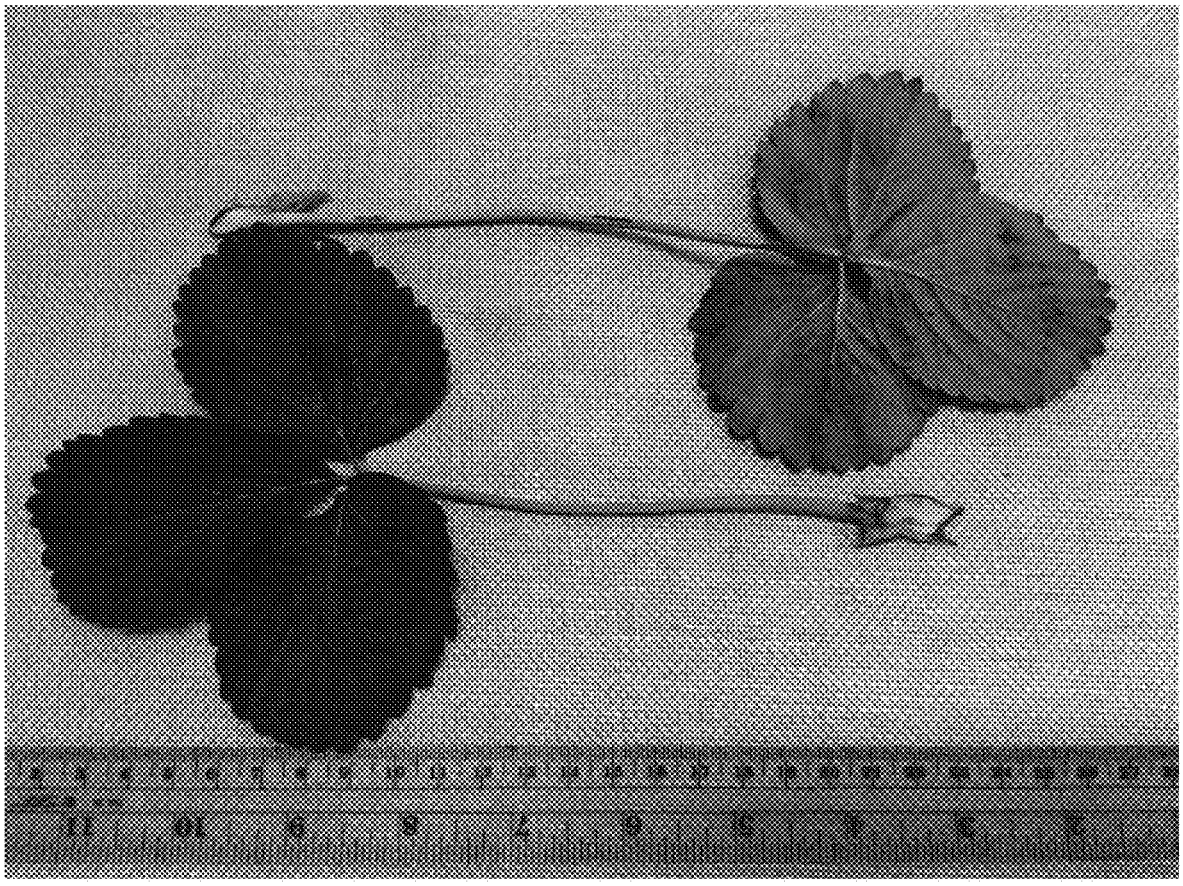
FIG. 4 shows upper and lower surfaces of leaf and leaf parts of 'BG-12.3266', taken in the month of April 2020.
Figure 5:
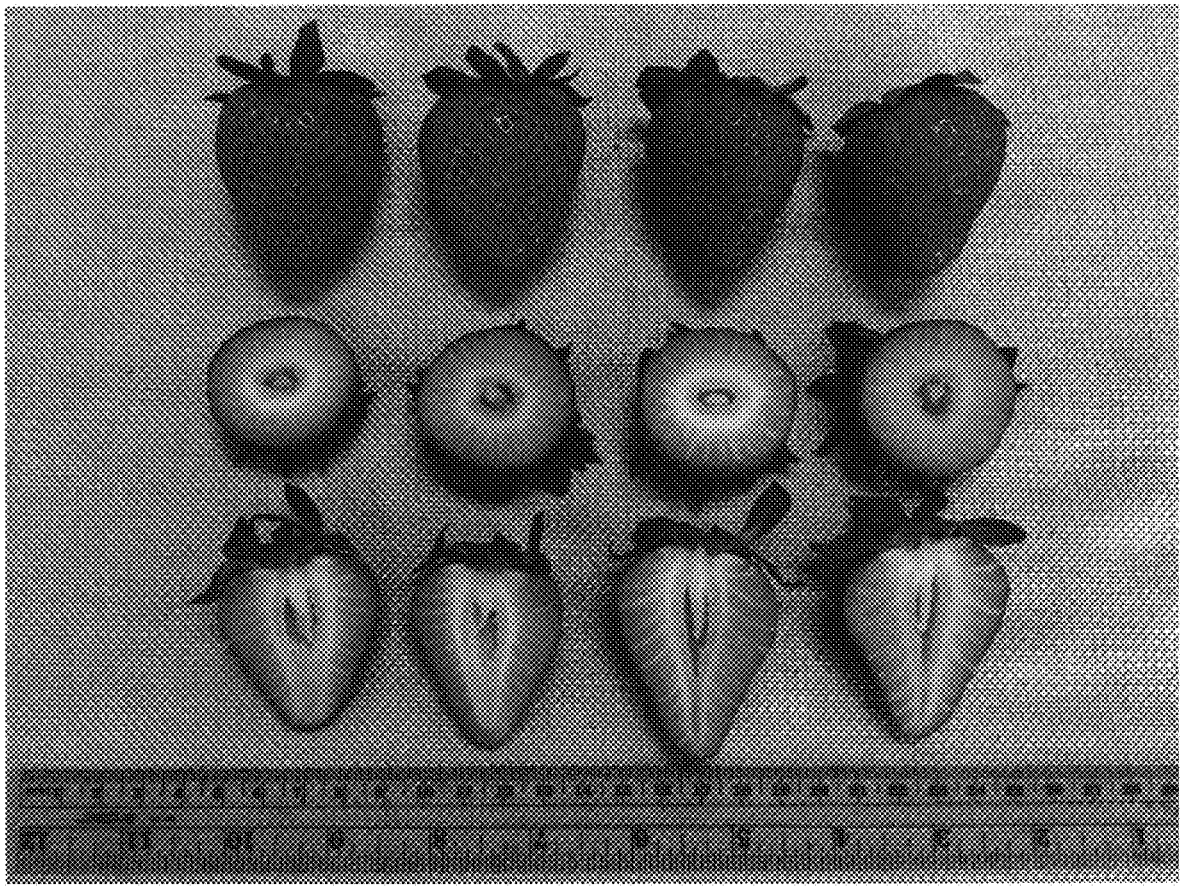
FIG. 5 shows internal and external mature fruit characteristics of 'BG-12.3266', taken in the month of April 2020.

The new variety 'BG-12.3266' has not been observed under all possible environmental conditions. The characteristics of the new variety 'BG-12.3266' may vary in detail, depending upon variations in environmental factors, including weather (temperature, humidity and light intensity), day length, soil type and location. In addition, the characteristics of any parental variety or comparison variety included in Tables 1, 2 and 3 of the present invention may vary in detail, depending upon variations in environmental factors, including weather (temperature, humidity and light intensity), day length, soil type and location.

The aforementioned photographs, together with the following description of the new variety 'BG-12.3266', unless otherwise noted, are based on observations taken during the 2020 growing season in Ventura County, Calif. These measurements and ratings were taken from plants of 'BG-12.3266' dug from a high-elevation nursery located in Siskiyou County, Calif. during early October 2019 and planted approximately four to five days later in Ventura County, Calif. The approximate age of the observed plants is five to six months. Yield observations including average weight and marketable yield, along with fruit quality characteristics including soluble solids, are averaged from five years of data collected from the 2016 through 2020 growing seasons. Flower measurements and characteristics are from secondary flowers unless otherwise noted. Fruit characteristics and measurements are from secondary fruit, unless otherwise noted.

Where noted, color terminology follows The Royal Horticultural Society Colour Chart, London (2007).

The following characteristics describe fruit, plant, stolon, foliage, fruiting truss, flower, reproductive organs and pest and disease characteristics of the new strawberry 'BG-12.3266'.

Fruit characteristics:

*Color of mature fruit*.—RHS 45B (ranges from orange red to red).

*Color of internal flesh (excluding core)*.—RHS 34C (light red).

*Color of core*.—RHS 39A (medium red).

*Average length (cm)*.—4.6.

*Average width (cm)*.—3.8.

*Size*.—Ranges from medium to large.

*Average length/width ratio*.—1.23 (ranges from slightly longer than broad to much longer than broad).

*Average calyx diameter (cm)*.—5.1.

*Season average weight (gm)*.—28.5.

*Achene color, shaded side*.—RHS 153D (yellow green group).

*Achene color, sun-exposed side*.—RHS 184A (greyed purple group).
*Average achene weight* (*mg*).—0.60.
*Average achenes per berry*.—347.
*Marketable yield season* (*gm/plant*).—1,079.
*Predominant shape*.—Cordate (cordiform).
*Difference in shape between primary and secondary fruit*.—Slight.
*Band without achenes*.—Absent or very narrow.
*Evenness of surface*.—Even or very slightly uneven.
*Evenness of color*.—Even or very slightly uneven.
*Glossiness*.—Strong.
*Insertion of achenes*.—Level with surface.
*Position of calyx attachment*.—Level.
*Attitude of sepals*.—Outward.
*Size of calyx in relation to fruit diameter*.—Slightly larger.
*Adherence of calyx* (*when fully ripe*).—Strong.
*Firmness of flesh*.—Very firm.
*Distribution of red color of the flesh*.—Marginal and central.
*Hollow center expression*.—Weak.
*Flavor*.—Good.
*Soluble solids* (*% Brix*).—8.6.
*Flowering season* (*50% of plants with at least one flower*).—Medium (December in Ventura County, Calif.).
*Maturing season* (*50% of plants with mature fruit*.—Medium (January in Ventura County, Calif.).
*Harvest period*.—January to May (in Ventura County, Calif.).
*Harvest maturity*.—Mid-season (in Ventura County, Calif.).
*Type of bearing*.—Not remontant.
*Shipping quality*.—Very good.
*Storage life at* 1-3 *degrees Celsius*.—7-10 days.
*Market use*.—Fresh.

Plant characteristics:
*Average height* (*cm*).—16.8.
*Average spread* (*cm*).—32.4.
*Size*.—Medium.
*Habit*.—Upright.
*Density*.—Medium.
*Vigor*.—Strong.
*Hardiness zones*.—9-10.

Stolon characteristics:
*Color*.—RHS 146C (yellow green group).
*Anthocyanin coloration*.—RHS 181B (greyed red group).
*Anthocyanin intensity*.—Medium.
*Pubescence*.—Medium.
*Attitude of hairs*.—Upward.
*Average quantity in nursery* (*per square foot*).—6 to 7 (medium).
*Average diameter at the first bract* (*mm*).—2.7 (thin).
*Length from mother plant to first daughter* (*cm*).—33.1.

Terminal leaflet characteristics:
*Average length* (*cm*).—7.5.
*Average width* (*cm*).—6.3.
*Average area terminal* ($cm^2$).—46.8.
*Average length/width ratio*.—1.19 (longer than broad).
*Shape of base*.—Obtuse.
*Margins* (*shape of teeth*).—Rounded (crenate).
*Average serrations per leaf*.—22.7.

Foliage characteristics:
*Color of upper surface*.—RHS 137B (medium yellow green).
*Color of underside*.—RHS 147C (yellow green group).
*Number of leaflets*.—3.
*Leaf size*.—Medium.
*Average length* (*cm*).—10.6.
*Average width* (*cm*).—13.7.
*Average area foliage* ($cm^2$).—145.4.
*Shape in cross section*.—Strongly to slightly concave.
*Interveinal blistering*.—Medium.
*Leaf glossiness*.—Medium.
*Leaf variegation*.—Absent.

Petiole characteristics:
*Petiole color*.—RHS 146C (yellow green group).
*Average length* (*cm*).—13.4.
*Average diameter* (*mm*).—2.9.
*Petiolule color*.—RHS 146C (yellow green group).
*Petiolule average length* (*mm*).—3.6.
*Attitude of hairs*.—Strongly outward.
*Frequency of bract leaflets*.—None (0% occurrence).
*Size of bract leaflets*.—N/A.
*Pubescence*.—Heavy.

Stipule characteristics:
*Color*.—RHS 146B (yellow green group).
*Anthocyanin coloration*.—RHS 62C (red purple group).
*Anthocyanin intensity*.—Absent or very weak.
*Average length* (*mm*).—13.2.
*Average width* (*mm*).—10.5.

Fruiting truss characteristics:
*Anthocyanin coloration*.—RHS 181C (greyed red group).
*Anthocyanin intensity*.—Weak.
*Average length at maturity* (*cm*).—22.3.
*Position relative to foliage*.—Beneath.
*Flower quantity* (*season average per plant*).—45 to 55 (medium).
*Average number of flowers per truss*.—Medium.
*Primary pedicel color*.—RHS 146C.
*Primary pedicel length* (*cm*).—18.3.
*Pedicel attitude of hairs*.—Upward.
*Pubescence*.—Weak.
*Attitude at first pick*.—Prostrate.

Flower characteristics:
*Petal color* (*upper surface*).—RHS NN155C (white group).
*Sepal color* (*upper surface*).—RHS 137B (green group).
*Corolla* (*flower*) *average diameter* (*mm*).—27.5 (medium).
*Calyx average diameter* (*mm*).—34.3.
*Petal average length* (*mm*).—10.4.
*Petal average width* (*mm*).—9.7.
*Petal average length/width ratio*.—1.07 (longer than broad).
*Average petals per flower*.—6.0.
*Sepal average length* (*mm*).—14.3.
*Sepal average width* (*mm*).—4.5.
*Sepal average length/width ratio*.—3.21.
*Average sepals per flower*.—12.3.
*Size of calyx relative to corolla*.—Larger.
*Size of inner calyx relative to outer calyx*.—Ranges from smaller to same.

*Relative position of petals* (*flowers with* 5 *or* 6 *petals*).—Ranges from touching to overlapping.

Reproductive organs:

*Receptacle/ovary color*.—RHS 147C (yellow green group).

*Anther/pollen color*.—RHS 14A (yellow orange group).

*Stamen*.—Present.

*Pollen amount*.—Abundant.

Disease and pest reactions:

*Powdery mildew* (*Sphaerotheca macularis*).—Moderately resistant.

*Angular leaf spot* (*Xanthomonas fragariae*).—Moderately susceptible.

*Botrytis fruit rot* (*Botrytis cinerea*).—Moderately susceptible.

*Fusarium wilt* (*Fusarium oxysporum*).—Susceptible.

*Anthracnose crown rot* (*Colletotrichum fragariae*).—Susceptible.

*Two-spotted spider mite* (*Tetranychus urticae*).—Moderately susceptible.

We claim:

1. A new and distinct strawberry plant named 'BG-12.3266', as herein described and illustrated.

* * * * *